United States Patent [19]  
Rivier et al.

[11] Patent Number: 4,784,987  
[45] Date of Patent: Nov. 15, 1988

[54] GRF ANALOGS VI

[75] Inventors: Jean E. F. Rivier; Wylie W. Vale, Jr., both of La Jolla, Calif.

[73] Assignee: The Salk Institute for Biological Studies, San Diego, Calif.

[21] Appl. No.: 60,149

[22] Filed: Jun. 10, 1987

Related U.S. Application Data

[63] Continuation-in-part of Ser. No. 2,723, Jan. 13, 1987, abandoned.

[51] Int. Cl.$^4$ ..................... A61K 37/43; C07K 7/10
[52] U.S. Cl. ........................................ 514/12; 530/324
[58] Field of Search ............................ 514/12; 530/324

[56] References Cited

U.S. PATENT DOCUMENTS 4,689,318  8/1987  Kaiser et al. ..................... 530/324

Primary Examiner—Delbert R. Phillips
Attorney, Agent, or Firm—Fitch, Even, Tabin & Flannery

[57] ABSTRACT

The invention provides peptides which are potent in stimulating the release of pituitary GH in fish and amphibians which have a substantial portion or all of the following sequence: $R_1$-$R_2$-$R_3$-$R_4$-$R_5$-Phe-$R_7$-$R_8$-$R_9$-Tyr-Arg-$R_{12}$-$R_{13}$-Leu-$R_{15}$-Gln-Leu-$R_{18}$-Ala-Arg-Lys-$R_{22}$-Leu-$R_{24}$-$R_{25}$-$R_{26}$-$R_{27}$-$R_{28}$-$R_{29}$-$R_{30}$-$R_{31}$-Gly-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-Ser wherein $R_1$ is N-Me Tyr, Tyr, desNH$_2$-Tyr, D-Tyr, N-Et Tyr, N-Ip Tyr, N-Me His, His, desNH$_2$-His, D-His, N-Et His, and N-Ip His; $R_2$ is Ala, D-Ala or D-NMA; $R_3$ is Asp or D-Asp; $R_4$ is Gly or Ala; $R_5$ and $R_{27}$ are selected from the group consisting of Met, Leu, Val, Nva, Gln, Thr, Ile, Ala, Arg, Asn, Asp, Cys, Glu, Gly, His, Nle, Lys, Phe, Pro, Ser, Tyr and Trp; $R_7$ is Asn or Thr; $R_8$ is Lys, Asn or Ser; $R_9$ is Ala or Ser; $R_{12}$ is Lys or Arg; $R_{13}$ is Ala, Val or Ile; $R_{15}$ is Gly or Ala; $R_{18}$ is Ser or Tyr; $R_{22}$ is Tyr or Leu; $R_{24}$ is His or Gln; $R_{25}$ is Thr, Asp, or Glu; $R_{26}$ is Leu or Ile; $R_{28}$ is Ala, Ser or Asn; $R_{29}$ is Lys or Arg; $R_{30}$ is Arg or Gln; $R_{31}$ is Val or Gln; $R_{33}$ is Gly or Glu; $R_{34}$ is Gly, Arg or Ser; $R_{35}$ is Ser or Asn; $R_{36}$ is Met, Leu, Val, Nva, Gln, Thr, Ile or Nle; $R_{37}$ is Ile or Glu; $R_{38}$ is Glu, Gln or Arg; $R_{39}$ is Asp, Arg or Gly; $R_{40}$ is Asp, Ser or Ala; $R_{41}$ is Asn, Arg or Lys; $R_{42}$ is Glu, Phe, Ala or Val; $R_{43}$ is Pro, Asn or Arg; $R_{44}$ is Leu or Ala; provided however that at least one of the following is present: $R_7$ is Asn, $R_8$ is Lys, $R_{13}$ is Ala, $R_{22}$ is Tyr and $R_{25}$ is Thr; and provided further that any or all of the residues after $R_{27}$ may be deleted. A 29-residue peptide beginning at the N-terminus may be preferred. These peptides, as well as their nontoxic salts, are considered to be particularly useful in aquiculture.

20 Claims, No Drawings

GRF ANALOGS VI

This invention was made with Government support under Grant No. AM-26741, awarded by the National Institutes of Health. The Government has certain rights in this invention.

This application is a continuation-in-part of application Ser. No. 2,723, filed Jan. 13, 1987.

The present invention relates to peptides having influence on the function of the pituitary gland in fish, birds and mammals. In particular, the present invention is directed to a peptide which promotes the release of growth hormone by the pituitary gland.

BACKGROUND OF THE INVENTION

Physiologists have long recognized that the hypothalamus controls the secretory functions of the adenohypophysis with the hypothalamus producing special substances which stimulate or inhibit the secretion of each pituitary hormone. A hypothalamic inhibitory factor was characterized in 1972 in the form of somatostatin which inhibits the secretion of growth hormone(GH). In 1982, human pancreatic (tumor) releasing factors (hpGRF) were isolated from extracts of human pancreatic tumors, purified, characterized, synthesized and tested, which were found to promote the release of GH by the pituitary. Both of these hypophysiotropic factors have been reproduced by total synthesis, and analogs of the native structures have been synthesized. It has been demonstrated that human hypothalamic GH releasing factor (GRF) has precisely the same structure. Corresponding hypothalamic GH releasing factors(GRFs) from the rat species, the porcine species, the ovine species, and the bovine and caprine species have also been characterized and synthesized.

SUMMARY OF THE INVENTION

Synthetic polypeptides have now been synthesized and tested which release GH from cultured pituitary cells and which are based upon the sequence of teleostei fish GRF and exhibit very substantially increased potency in fish. These peptides may be from 27 to 44 residues in length, being shortened from the C-terminus, the carboxyl moiety of which may be free acid, amide or otherwise substituted.

Compositions in accordance with the invention include such peptides which are between about 27 and 44 residues in length, or a nontoxic salt of any of these, dispersed in a pharmaceutically or veterinarily acceptable liquid or solid carrier. Such compositions can be used to promote the growth of warm-blooded animals, including fowl, and particularly in aquiculture for cold-blooded animals, e.g. fish, eels, etc.

In one preferred embodiment, the invention provides a peptide which can be prepared by chemical synthesis and which is useful in accelerating growth in fish or other cold-blooded animals, which peptide has the formula: $R_1$-$R_2$-$R_3$-Gly-$R_5$-Phe-Asn-Lys-Ala-Tyr-Arg-Lys-Ala-Leu-$R_{15}$-Gln-Leu-Ser-Ala-Arg-Lys-Tyr-Leu-His-Thr-Leu-$R_{27}$-$R_{28}$-$R_{29}$-$R_{30}$-$R_{31}$-NHR wherein $R_1$ is N-Me Tyr, N-Me His, N-Et Tyr, N-Et His, N-Ip His or N-Ip Tyr; $R_2$ is Ala or D-Ala; $R_3$ is Asp or D-Asp; $R_5$ is Met, Nva or Nle; $R_{15}$ is Gly or Ala; $R_{27}$ is Nva or Nle; $R_{28}$ is Ala, Ser, Asn or des-$R_{28}$; $R_{29}$ is Lys or Arg or des-$R_{29}$; $R_{30}$ is Arg or Gln or des-$R_{30}$; and $R_{31}$ is Val or Gln or des-$R_{31}$; and R is H or lower alkyl.

In another preferred embodiment, the invention provides peptides which are useful in accelerating growth in fish or other cold-blooded animals, which peptides have the formula: H-His-D-Ala-Asp-Gly-$R_5$-Phe-Asn-Lys-Ala-Tyr-Arg-Lys-Ala-Leu-Gly-Gln-Leu-Ser-Ala-Arg-Lys-Tyr-Leu-His-Thr-Leu-R-$R_{27}$-$R_{28}$-$R_{29}$-$R_{30}$-$R_{31}$-NHR wherein $R_5$ is Met, Nle, Ile or Leu; $R_{27}$ is Met, Nle, Ile or Leu; $R_{28}$ is Ala, Ser, Asn or des-$R_{28}$; $R_{29}$ is Lys or Arg or des-$R_{29}$; $R_{30}$ is Arg or Gln or des-$R_{30}$; $R_{31}$ is Val or Gln or des-$R_{31}$; and R is H or lower alkyl.

In still another preferred embodiment, the invention provides peptides which is useful in accelerating growth in fish or other cold-blooded animals, which peptides have the formula: H-His-Ala-D-Asp-Gly-$R_5$-Phe-Asn-Lys-Ala-Tyr-Arg-Lys-Ala-Leu-Gly-Gln-Leu-Ser-Ala-Arg-Lys-Tyr-Leu-His-Thr-Leu-R $_{27}$-Ala-Lys-Arg-Val-Gly-Gly-Gly-Ser-$R_{36}$-Ile-Glu-Asp-Asp-Asn-Glu-Pro-Leu-Ser-NH$_2$ wherein $R_5$, $R_{27}$ and $R_{36}$ are selected from Met, Nle and Leu.

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminus appears to the left and the carboxyl group at the C-terminus to the right. Natural amino acids are those common, naturally occurring amino acids that are found in proteins and are referred to by their accepted abbreviations: Gly, Ala, Val, Leu, Ile, Ser, Thr, Lys, Arg, Asp, Asn, Glu, Gln, Cys, Met, Phe, Tyr, Pro, Trp and His. By Nle is meant norleucine, and by Nva is meant norvaline. Where the amino acid residue has isomeric forms, it is the L-form of the amino acid that is represented unless otherwise expressly indicated. By Me is meant methyl, by Et is meant ethyl and by Ip is meant isopropyl. By D-NMA is meant N-Me D-Ala, and by lower alkyl is meant a carbon chain having from 1 to 4 carbon atoms.

The invention provides peptides having the following sequence (I): $R_1$-$R_2$-$R_3$-$R_4$-$R_5$-Phe-$R_7$-$R_8R_9$-Tyr-Arg-$R_{12}$-$R_{13}$-Leu-$R_{15}$-Gln-Leu-$R_{18}$-Ala-Arg-Lys-$R_{22}$-Leu-$R_{24}$-$R_{25}$-$R_{26}$-$R_{27}$-$R_{28}$-$R_{29}$-$R_{30}$-$R_{31}$-Gly-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$ Ser wherein $R_1$ is N-Me Tyr, Tyr, desNH$_2$-Tyr, D-Tyr, N-Et Tyr, N-Ip Tyr, N-Me His, His, desNH$_2$-His, D-His, N-Et His, and N-Ip His; $R_2$ is Ala, D-Ala or D-NMA; $R_3$ is Asp or D-Asp; $R_4$ is Gly or Ala; $R_5$ and $R_{27}$ are selected from the group consisting of Met, Leu, Val, Nva, Gln, Thr, Ile, Ala, Arg, Asn, Asp, Cys, Glu, Gly, His, Nle, Lys, Phe, Pro, Ser, Tyr and Trp; $R_7$ is Asn or Thr; $R_8$ is Lys, Asn or Ser; $R_9$ is Ala or Ser; $R_{12}$ is Lys or Arg; $R_{13}$ is Ala, Val or Ile; $R_{15}$ is Gly or Ala; $R_{18}$ is Ser or Tyr; $R_{22}$ is Tyr or Leu; $R_{24}$ is His or Gln; $R_{25}$ is Thr, Asp, or Glu; $R_{26}$ is Leu or Ile; $R_{28}$ is Ala, Ser or Asn; $R_{29}$ is Lys or Arg; $R_{30}$ is Arg or Gln; $R_{31}$ is Val or Gln; $R_{33}$ is Gly or Glu; $R_{34}$ is Gly, Arg or Ser; $R_{35}$ is Ser or Asn; $R_{36}$ is Met, Leu, Val, Nva, Gln, Thr, Ile or Nle; $R_{37}$ is Ile or Glu; $R_{38}$ is Glu, Gln or Arg; $R_{39}$ is Asp, Arg or Gly; $R_{40}$ is Asp, Ser or Ala; $R_{41}$ is Asn, Arg or Lys; $R_{42}$ is Glu, Phe, Ala or Val; $R_{43}$ is Pro, Asn or Arg; $R_{44}$ is Leu or Ala; provided however that at least one of the following is present: $R_7$ is Asn, $R_8$ is Lys, $R_{13}$ is Ala, $R_{22}$ is Tyr and $R_{25}$ is Thr; and provided further that any or all of the residues after $R_{27}$ may be deleted.

Fragments of the peptide sequence (I) which extend from the N-terminus through residue-27 have biological potency in effecting the release of GH by the pituitary, and such biologically active fragments are considered as falling within the scope of the overall invention. When the peptide fragment extends only to residue 27 or 28, the carboxyl moiety at C-terminus should be —$CONH_2$ or a substituted lower alkyl amide. When the fragment extends to one of residues 29 thru 39, the carboxyl moiety at C-terminus is preferably an amide or a substituted amide but may be —COOH. When the fragment has 40 or more residues, there is no clear preference for the carboxyl moiety at the C-terminus.

The peptides are synthesized by a suitable method, such as by exclusively solid-phase techniques, by partial solid-phase techniques, by fragment condensation or by classical solution couplings. The employment of recently developed recombinant DNA techniques may be used to prepare a portion of a peptide containing only natural amino acid residues, which could then be linked to a short terminal peptides. For example, techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. Classical solution synthesis is described in detail in the treatise "Methoden der Organischen Chemie (Houben-Weyl): Synthese von Peptiden", E. Wunsch (editor) (1974) Georg Thieme Verlag, Stuttgart, W. Ger. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Also considered to be within the scope of the present invention are intermediates of the formula (II): X-$R_1(X^1$ or $X^2)$-$R_2$-$R_3(X^3)$-$R_4$-$R_5(XX)$-Phe-$R_7(X^4$ or $X^5)$-$R_8(X^4,\ X^5$ or $X^7)$-$R_9(X^4)$-Tyr$(X^2)$-Arg$(X^6)$-$R_{12}(X^6$ or $X^7)$-$R_{13}$-Leu-$R_{15}$-Gln$(X^5)$-Leu-$R_{18}(X^2$ or $X^4)$-Ala-Arg$(X^6)$-Lys $(X^7)$-$R_{22}(X^2)$-Leu-$R_{24}(X^1$ or $X^5)$-$R_{25}(X^3$ or $X^4)$-$R_{26}$-$R_{27}(XX)$-$R_{28}(X^4$ or $X^5)$-$R_{29}$-$(X^6$ or $X^7)$-$R_{30}(X^5$ or $X^6)$-$R_{31}(X^5)$-Gly-$R_{33}(X^3)$-$R_{34}(X^4$ or $X^6)$-$R_{35}(X^4$ or $X^5)$-$R_{36}(X^3$ or $X^4)$-$R_{37}(X^3)$-$R_{38}(X^3$ or $X^5$ or $X^6)$-$R_{39}(X^3$ or $X^6)$-$R_{40}(X^3$ or $X^4)$-$R_{41}(X^5$ or $X^6$ or $X^7)$-$R_{42}(X^3)$-$R_{43}(X^5$ or $X^6)$-$R_{44}$-Ser$(X^4)$-$X^8$ wherein:

X is either hydrogen or an a-amino protecting group. The a-amino protecting groups contemplated are those well known to be useful in the art of stepwise synthesis of polypeptides. Among the classes of a-amino protecting groups which may be employed are (1) aromatic urethan-type protecting groups, such as fluorenylmethyloxycarbonyl (FMOC), benzyloxycarbonyl(Z) and substituted Z, such as p-chlorobenzyloxycarbonyl, p-nitrobenzyloxycarbonyl, p-bromobenzyloxycarbonyl, and p-methoxybenzyloxycarbonyl; (2) aliphatic urethan protecting groups, such as t-butyloxycarbonyl (BOC), diisopropylmethyloxycarbonyl, isopropyloxycarbonyl, ethoxycarbonyl, allyloxycarbonyl; and (3) cycloalkyl urethan-type protecting groups, such as cyclopentyloxycarbonyl, adamantyloxycarbonyl, and cyclohexyloxycarbonyl. If the residue in the 1-position contains an N-alkyl substitution, it can be used as the protecting group, or it can be added following removal of the protecting group, e.g. BOC. The preferred a-amino protecting group is BOC.

$X^1$ is hydrogen or a protecting group for the imidazole nitrogen of His, such as benzyloxymethyl or Tos.

$X^2$ may be a suitable protecting group for the phenolic hydroxyl group of Tyr, such as tetrahydropyranyl, tert-butyl, trityl, Bzl, CBZ, 4Br-CBZ and 2,6-dichlorobenzyl(DCB). The preferred protecting group is 2,6-dichlorobenzyl. $X^2$ can be hydrogen which means that there is no side-chain protecting group on the amino acid residue in that position.

$X^3$ is hydrogen or a suitable ester-forming protecting group for the carboxyl group of Asp or Glu, such as benzyl(Bzl), 2,6-dichlorobenzyl, methyl, cyclohexyl or ethyl.

$X^4$ may be a suitable protecting group for the hydroxyl group of Thr or Ser, such as acetyl, benzoyl(Bz), tert-butyl, trityl, tetrahydropyranyl, Bzl, 2,6-dichlorobenzyl and CBZ. The preferred protecting group is Bzl. $X^4$ can be hydrogen, which means there is no protecting group on the hydroxyl group.

$X^5$ is hydrogen or a suitable protecting group for the side chain amido group of Asn or Gln. It is preferably xanthyl(Xan).

$X^6$ is a suitable protecting group for the guanido group of Arg, such as nitro, Tos, CBZ, adamantyloxycarbonyl, and BOC, or is hydrogen.

$X^7$ is hydrogen or a suitable protecting group for the side chain amino group of Lys. Illustrative of suitable side chain amino protecting groups are 2-chlorobenzyloxycarbonyl(2-Cl-Z), Tos, t-amyloxycarbonyl and BOC.

XX is a suitable side-chain protecting group selected from those described above or is hydrogen.

Met can optionally be protected by oxygen, but is preferably left unprotected.

The selection of a side chain amino protecting group is not critical except that generally one is chosen which is not removed during deprotection of the a-amino groups during the synthesis. However, for some amino acids, e.g. His, protection is not generally necessary after coupling is completed, and the protecting groups may be the same.

$X^8$ is a suitable protecting group for the C-terminal carboxyl group, such as the ester-forming group $X^3$, or is an anchoring bond used in solid-phase synthesis for linking to a solid resin support, or is des-$X^8$, in which case the residue at the C-terminus has a carboxyl moiety as defined hereinbefore, i.e. free acid, amide or substituted amide. When a solid resin support is used, it may be any of those known in the art, such as one having the formulae: —O—$CH_2$-resin support, —NH-benzhydrylamine (BHA) resin support or —NH-paramethylbenzhydrylamine (MBHA) resin support. When the unsubstituted amide is desired, use of BHA or MBHA resin is preferred, because cleavage directly gives the amide. In case the N-methyl amide is desired, it can be generated from an N-methyl BHA resin. Other substituted amides can be synthesized by the procedure set forth in W. Kornreich et al. *Int. J. Peptide Protein Res.*, 25 (1985) 414–420. Should groups other than the free acid be desired at the C-terminus, it may be preferable to sythesize the peptide using classical methods as set forth in the Houben-Weyl text.

In the formula for the intermediate, at least one of the X-groups is a protecting group or $X^8$ includes resin support. Thus, the invention also provides a method for manufacturing a peptide of interest by (a) forming a peptide having at least one protective group and the formula (II): wherein: X, $X^1$, $X^2$, $X^3$, $X^4$, $X^5$, $X^6$, $X^7$ and XX are each either hydrogen or a protective group and $X^8$ is either a protective group or an anchoring bond to resin support or is des-$X^8$, in which case the residue at the C-terminus has a carboxy moiety as defined hereinbefore; (b) splitting off the protective group or groups or anchoring bond from the peptide of the formula (II); and (c) if desired, converting the resulting peptide of the sequence (I) into a nontoxic salt thereof.

In selecting a particular side chain protecting group to be used in the synthesis of the peptides, the following general rules are followed: (a) the protecting group preferably retains its protecting properties and is not split off under coupling conditions, (b) the protecting group should be stable to the reagent and, with the exception of Xan, is preferably stable under the reaction conditions selected for removing the a-amino protecting group at each step of the synthesis, and (c) the side chain protecting group must be removable, upon the completion of the synthesis of the desired amino acid sequence, under reaction conditions that will not undesirably alter the peptide chain.

If the peptides contain all naturally occurring residues, they may be prepared using recombinant DNA technology. When peptides are not prepared using recombinant DNA technology, they are preferably prepared using solid phase synthesis, such as that generally described by Merrifield, *J. Am. Chem. Soc.*, 85, p 2149 (1963), although other equivalent chemical syntheses known in the art can also be used as previously mentioned. Solid-phase synthesis is commenced from the C-terminus of the peptide by coupling a protected a-amino acid to a suitable resin. Such a starting material can be prepared by attaching an a-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis," Pierce Chemical Co., Rockford, Ill. (1984), Chapter 1. As specified in this text, BHA and MBHA resin supports are commercially available and are generally used only when the desired peptide being synthesized has an unsubstituted amide at the C-terminus.

The C-terminal amino acid, e.g. Leu, protected by BOC, can be first coupled to the chloromethylated resin according to the procedure set forth in *Chemistry Letters*, K. Horiki et al. 165-168 (1978), using KF in DMF at about 60° C. for 24 hours with stirring, when the 44-residue peptide free acid is to be synthesized. Following the coupling of the BOC-protected amino acid to the resin support, the a-amino protecting group is removed, as by using trifluoroacetic acid(TFA) in methylene chloride or TFA alone. The deprotection is carried out at a temperature between about 0° C. and room temperature. Other standard cleaving reagents, such as HCl in dioxane, and conditions for removal of specific a-amino protecting groups may be used as described in Schroder & Lubke, "The Peptides", 1 pp 72-75 (Academic Press 1965).

After removal of the a-amino protecting group, the remaining a-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke supra, in Chapter III and by Kapoor, *J. Phar. Sci.*, 59, pp 1-27 (1970).

Each protected amino acid or amino acid sequence is introduced into the solid phase reactor in about a fourfold or more excess, and the coupling may be carried out in a medium of dimethylformamide(DMF): $CH_2Cl_2$ (1:1) or in DMF or $CH_2Cl_2$ alone. In cases where incomplete coupling occurs, the coupling procedure is repeated before removal of the a-amino protecting group prior to the coupling of the next amino acid. The success of the coupling reaction at each stage of the synthesis, if performed manually, is preferably monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers*, 1978, 17, pp 1927-1938.

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups $X^1$, $X^2$, $X^3$, $X^4$, $X^5$, $X^6$ and $X^7$ and the anchoring bond $X^8$ and also the a-amino protecting group X if one is used, to obtain the peptide in the form of the free acid. If Met is present in the sequence, the BOC protecting group is preferably first removed using trifluoroacetic acid(TFA)/ethanedithiol prior to cleaving the peptide from the resin with HF to eliminate potential S-alkylation. When using hydrogen fluoride for cleaving, anisole, p-cresol, methylethyl sulfide and/or and other known scavengers are preferably included in the reaction vessel.

The following Example sets forth a preferred method for synthesizing peptides by the solid-phase technique. It will of course be appreciated that the synthesis of a correspondingly shorter peptide fragment is effected in the same manner by merely eliminating the requisite number of amino acids at either end of the chain; however, it is presently felt that biologically active fragments should contain the indicated sequence at the N-terminus.

EXAMPLE I

The synthesis of the peptide having the formula: N-Me-His-Ala-Asp-Gly-Met-Phe-Asn-Lys-Ala-Tyr-Arg-Lys-Ala-Leu-Gly-Gln-Leu-Ser-Ala-Arg-Lys-Tyr-Leu-His-Thr-Leu-Met-Ala-Lys-Arg-Val-Gly -Gly-Gly-Ser-Met-Ile-Glu-Asp-Asp-Asn-Glu-Pro-Leu-Ser-NH$_2$ is conducted in a stepwise manner using a Beckman 990 peptide synthesizer on an MBHA resin having a substitution range of about 0.1 to 0.5 mmoles/g. resin. Coupling of BOC-Ser(Bzl) to the resin is performed by the general procedure set forth in Vale et al. U.S. Pat. No. 4,292,313, using a threefold excess, in CH$_2$Cl$_2$ with DCC as an activating reagent for 2 hours with stirring. It results in the substitution of about 0.2–0.6 mmol. Ser per gram of resin.

After deblocking and neutralization, the peptide chain is built step-by-step on the resin. Deblocking, neutralization and addition of each amino acid is performed in general accordance with the procedure set forth in detail in Rivier, J, *J. Amer. Chem. Soc.*, 96, 2986–2992 (1974). All solvents that are used are carefully degassed by sparging with an inert gas, e.g. helium or nitrogen, to insure the absence of oxygen that might undesirably oxidize the sulfur of the Met residue.

Deblocking is preferably carried out in accordance with Schedule A which follows:

| SCHEDULE A | |
|---|---|
| Reagent | Mixing time (Min.) |
| 1. 60% TFA/2% ethanedithiol | 10 |
| 2. 60% TFA/2% ethanedithiol | 15 |
| 3. IPA/1% ethanedithiol | 0.5 |
| 4. Et$_3$N (10%) in CH$_2$Cl$_2$ | 0.5 |
| 5. MeOH | 0.5 |
| 6. Et$_3$N (10%) in CH$_2$Cl$_2$ | 0.5 |
| 7. MeOH (twice) | 0.5 |
| 8. CH$_2$Cl$_2$ (twice) | 0.5 |

The couplings are preferably carried out as set out in Schedule B which follows:

| SCHEDULE B | |
|---|---|
| Reagent | Mixing time (Min.) |
| 9. DCCI | — |
| 10. Boc-amino acid | 50–90 |
| 11. MeOH (twice) | 0.5 |
| 12. CH$_2$Cl$_2$ (twice) | 0.5 |
| 13. Ac$_2$O (3M) in CH$_2$Cl$_2$ | 15.0 |
| 14. CH$_2$Cl$_2$ | 0.5 |
| 15. MeOH | 0.5 |
| 16. CH$_2$Cl$_2$ (twice) | 0.5 |

Briefly, one to two mmol. of BOC-protected amino acid in methylene chloride is used per gram of resin, plus one equivalent of 1.0 molar DCCI in methylene chloride for two hours. When BOC-Arg(Tos) is being coupled, a mixture of 50% DMF and methylene chloride is used. Bzl ether is used as the hydroxyl side-chain protecting group for Ser and Thr. The amido group of Asn or Gln is protected by Xan when DCC coupling is used as is preferred. P-nitrophenyl ester(ONp) may also be used to activate the carboxyl end of Asn or Gln, and for example, BOC-Asn(ONp) can be coupled overnight using one equivalent of HOBt in a 50% mixture of DMF and methylene chloride, in which case no DCC is added. 2-chloro-benzyloxycarbonyl(2Cl-Z) is used as the protecting group for the Lys side chain. Tos is used to protect the guanido group of Arg and the imidazole nitrogen of His, and the Glu or Asp side-chain carboxyl group is protected with OBzl. The phenolic hydroxyl group of Tyr is protected with 2,6-dichlorobenzyl(DCB). At the end of the synthesis, the following composition is obtained: BOC-N-Me-His(X$^1$)-Ala-Asp(X$^3$)-Gly-Met-Phe-Asn(X$^4$)-Lys(X$^7$)-Ala-Tyr(X$^2$)-Arg(X$^6$)-Lys(X$^7$)-Ala-Leu-Gly-Gln(X$^5$)-Leu-Ser) X$^4$)-Ala-Arg(X$^6$)-Lys(X$^7$)-Tyr(X$^2$)-Leu-His(X$^1$)-Thr(X$^4$)-Leu-Met-Ala-Lys(X$^7$)-Arg(X$^6$)-Val-Gly-Gly-Gly-Ser(X$^4$)-Met-Ile-Glu(X$^3$)-Asp(X$^3$)-Asp(X$^3$)-Asn(X$^4$)-Glu(X$^3$)-Pro-Leu-Ser(Bzl)-X$^8$ wherein X$^1$ is Tos, X$^2$ is DCB, X$^3$ is Bzl, X$^4$ is Bzl, X$^5$ is Xan, X$^6$ is Tos, X$^7$ is 2Cl—Z and X$^8$ is —NH-resin support. Xan may have been partially or totally removed by TFA treatment used to deblock the a-amino protecting group.

In order to cleave and deprotect the protected peptide-resin, it is treated with 1.5 ml. anisole, 0.5 ml. methylethylsulfide and 15 ml. hydrogen fluoride(HF) per gram of peptide-resin, at −20° C. for one-half hour and at 0.° C. for one-half hour. After elimination of the HF under high vacuum, the resin-peptide remainder is washed alternately with dry diethyl ether and chloroform, and the peptide is then extracted with degassed 2N aqueous acetic acid, or water, and separated from the resin by filtration.

The cleaved and deprotected peptide is then dissolved in 0–5% acetic acid and subjected to purification which may include Sephadex G-50 fine gel filtration.

The peptide is then further purified by preparative or semi-preparative HPLC as described in Rivier et al., *Peptides: Structure and Biological Function*, (1979) pp 125–8 and Marki et al. *J. Am. Chem. Soc.* 103, 3178 (1981). Cartridges fitting Waters Associates prep LC-500 are packed with 15–20 micron C$_{18}$ Silica from Vydac (300A). A gradient of CH$_3$CN in TEAP is generated by a low pressure Eldex gradient maker, as described in Rivier, J., *J. Liq. Chromatography* 1, 343–367 (1978). The chromatographic fractions are carefully monitored by HPLC, and only the fractions showing substantial purity are pooled. Desalting of the purified fractions, independently checked for purity, is achieved using a gradient of CH$_3$CN in 0.1% TFA. The center cut is then lyophilized to yield the desired peptide, the purity of which can be greater than 98%.

The synthesis is repeated using a chloromethylated resin to produce the same peptide having a free acid C-terminus using an initial procedure as generally described in *Chemistry Letters*, supra, to link Leu to the resin.

EXAMPLE II

The synthesis of a 29-residue amidated peptide having the formula: N-Et-Tyr-Ala-D-Asp-Gly-Met-Phe-Asn-Lys-Ala-Tyr-Arg-Lys-Ala-Leu-Gly-Gln-Leu-Ser-Ala-Arg-Lys-Tyr-Leu-His-Thr-Leu-Met-Ala-Lys -NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC.

EXAMPLE III

The synthesis of a peptide having the formula: N-Et-His-Ala-Asp-Gly-Nle-Phe-Asn-Lys-Ala-Tyr-Arg-Lys-Ala-Leu-Gly-Gln-Leu-Ser-Ala-Arg-Lys-Tyr-Leu-His-Thr-Leu-Nle-Ala-Lys-Arg-Val-Gly-Glu-Ser-Asn-Gln-Glu-Arg-Gly-Ser-Lys-Ala-Arg-Ala-OH is conducted in a stepwise manner using a Beckman 990 Peptide Synthesizer on a chloromethylated resin. The peptide is judged to be substantially pure using TLC and HPLC.

EXAMPLE IV

The synthesis of the GRF analog peptide having the formula: N-Ip-His-Ala-Asp-Gly-Met-Phe-Asn-Lys-Ala-Tyr-Arg-Lys-Ala-Leu-Gly-Gln-Leu-Ser-Ala-Arg-Lys-Tyr-Leu-His-Thr-Leu-Nle-Ala-Lys-Arg-Val-NH$_2$ is conducted in a stepwise manner using a Beckman 990 Peptide Synthesizer on an MBHA resin as in Example I. The peptide is judged to be substantially pure using TLC and HPLC.

EXAMPLE V

The synthesis of a peptide having the formula: H-His-D-Ala-Asp-Gly-Nle-Phe-Asn-Lys-Ala-Tyr-Arg-Lys-Ala-Leu -Gly-Gln-Leu-Ser-Ala-Arg-Lys-Tyr-Leu-His-Thr-Leu-Met-Ala -Lys-Arg-Val-Gly-Gly-Gly-Asn-Met-Ile-Glu-Arg-Ser-Arg-Val -Asn-NH$_2$ is conducted in a stepwise manner using a Beckman 990 Peptide Synthesizer on an MBHA rssin as in Example I. The peptide is judged to be substantially pure using TLC and HPLC.

EXAMPLE VI

The synthesis of a peptide having the formula: N-Me-Tyr-Ala-Asp-Gly-Nle-Phe-Asn-Lys-Ala-Tyr-Arg-Lys-Ala-Leu-Gly-Gln-Leu-Ser-Ala-Arg-Lys-Tyr-Leu-His--Thr-Leu-Nle-Ala-Lys--NHCH$_2$CH$_3$ is conducted using the same general procedure as set forth in Example I but employing an N-alkylamine resin, also termed an N-ethylaminomethyl resin (NEAM resin), as described in U.S. Pat. No. 4,569,967 issued Feb. 11, 1986 in the name of W. D. Kornreich, the disclosure of which is incorporated herein by reference. About 10 grams of the chloromethylated resin of Example I are reacted with 100 ml. of ethylamine at about 4° C. for about 24 hours with continuous stirring to change the a-chlorobenzyl groups to N-ethyl a-aminobenzyl groups, upon which the peptide is then built via an initial, substituted-amide linkage.

Upon completion of the desired peptide sequence, deprotection and cleavage from the resin are effected by treatment with HF with anisole as a scavenger, stirring first at 0° C. and then allowing the stirred mixture to slowly warm to room temperature over about 3 hours, a procedure which cleaves the peptide from the resin as the ethylamide. Amino acid analysis shows that the desired peptide structure is obtained. The peptide is judged to be substantially pure using TLC and HPLC.

EXAMPLE VII

The peptide having the formula: N-Et-His-Ala-Asp-Gly-Met-Phe-Asn-Lys-Ala-Tyr-Arg-Lys-Ala-Leu-Ala-Gln-Leu-Ser-Ala-Arg-Lys-Tyr-Leu-His-Thr-Leu-Met-Ala-Lys-NHCH$_3$ is synthesized using the same general procedure as set forth in Example VI but employing methylamine instead of ethylamine to form the N-methylaminomethyl resin (NMAM resin) upon which the peptide is built. Cleavage and deprotection using HF yields the deprotected N-methylamide. Amino acid analysis shows that the desired peptide structure is obtained.

EXAMPLE VIII

The peptide having the formula: H-His-Ala-Asp-Ala-Nle-Phe-Asn-Lys-Ala-Tyr-Arg-Lys-Ala-Leu-Gly-Gln-Leu-Ser -Ala-Arg-Lys-Tyr-Leu-His-Thr-Leu-Met-Ala-Lys-Arg-Val-NHCH$_2$CF$_3$ is synthesized using the same general procedure as set forth in Example VI but employing trifluoroethylamine.HCl instead of ethylamine to form the N-trifluoroethylaminomethyl resin (NTFEAM resin) on which the peptide is built. Cleavage and deprotection using HF yields the deprotected N-trifluoroethylamide. The peptide is judged to be substantially pure using TLC and HPLC.

EXAMPLE IX

The synthesis of a peptide having the formula: H-His-Ala-Asp-Gly-Met-Phe-Asn-Lys-Ala-Tyr-Arg-Lys-Ala-Leu-Gly-Gln-Leu-Tyr-Ala-Arg-Lys-Tyr-Leu-His-Thr-Leu-Met-Ala-Lys-Arg-Val-Gly-Glu-Ser-Asn-Leu-Glu-Gln-Arg-Ala-Arg-Val-Asn-Leu-NH$_2$ is conducted in a stepwise manner using a Beckman 990 Peptide Synthesizer on an MBHA resin as generally described in Vale et al. U.S. Pat. No. 4,292,313. The peptide is judged to be substantially pure using TLC and HPLC. The acetate salt is then prepared by dissolving the peptide in water and adding 1N acetic acid. The resulting solution is lyophilized to yield the acetic acid salt.

EXAMPLE X

The synthesis of the GRF analog peptide having the formula: H-His-Ala-Asp-Gly-Ile-Phe-Asn-Lys-Ala-Tyr-Arg-Lys-Ala-Leu-Gly-Gln-Leu-Ser-Ala-Arg-Lys-Leu-Leu-His-Thr-Leu-Val-Ala-Lys-NH$_2$ is conducted in a stepwise manner using a Beckman 990 Peptide Synthesizer on an MBHA resin as in Example I. The peptide is judged to be substantially pure using TLC and HPLC.

EXAMPLE XI

The synthesis of the GRF analog peptide having the formula: H-His-Ala-Asp-Gly-Leu-Phe-Asn-Lys-Ala-Tyr-Arg-Lys-Ala-Leu-Gly-Gln-Leu-Ser-Ala-Arg-Lys-Tyr-Leu-Gln-Thr-Leu-Nle-Ala-Lys-Arg-Val-Gly-NH$_2$ is conducted in a stepwise manner using a Beckman 990 Peptide Synthesizer on an MBHA resin as in Example I. The peptide is judged to be substantially pure using TLC and HPLC.

EXAMPLE XII

The synthesis of the GRF analog peptide having the formula: H-His-Ala-Asp-Gly-Met-Phe-Asn-Lys-Ser-Tyr-Arg-Lys-Ala-Leu-Gly-Gln-Leu-Ser-Ala-Arg-Lys-Tyr-Leu-His-Glu-Leu-Ile-Ala-Lys-Arg-Val-Gly-NH$_2$ is conducted in a stepwise manner using a Beckman 990 Peptide Synthesizer on an MBHA resin as in Example I. The peptide is judged to be substantially pure using TLC and HPLC.

EXAMPLE XIII

The synthesis of the GRF analog peptide having the formula: desNH$_2$-His-Ala-Asp-Gly-Val-Phe-Asn-Lys-Ala-Tyr-Arg-Arg-Val-Leu-Gly-Gln-Leu-Ser-Ala-Arg-Lys-Tyr-Leu -His-Thr-Leu-Gln-Ala-Lys-NH$_2$ is conducted in a stepwise manner using a Beckman 990 Peptide Synthesizer on an MBHA resin as in Example I. The peptide is judged to be substantially pure using TLC and HPLC.

EXAMPLE XIV

The synthesis of the GRF analog peptide having the formula: N-Me-His-D-NMA-Asp-Gly-Pro-Phe-Asn- Lys-Ala-Tyr-Arg-Lys-Ala-Leu-Gly-Gln-Leu-Ser-Ala-Arg-Lys-Tyr-Leu-His -Thr-Leu-Thr-Ala-Lys-NH$_2$ is conducted in a stepwise manner using a Beckman 990 Peptide Synthesizer on an MBHA resin as in Example I. The peptide is judged to be substantially pure using TLC and HPLC.

EXAMPLE XV

The synthesis of the GRF analog peptide having the formula: H-His-D-NMA-Asp-Gly-Nva-Phe-Asn-Lys-Ala-Tyr-Arg-Lys-Ala-Leu-Gly-Gln-Leu-Ser-Ala-Arg-Lys-Tyr-Leu-His-Thr-Leu-Phe-Ala-Lys-Arg-Val-NH$_2$ is conducted in a stepwise manner using a Beckman 990 Peptide Synthesizer on an MBHA resin as in Example I. The peptide is judged to be substantially pure using TLC and HPLC.

EXAMPLE XVI

The synthesis of the GRF analog peptide having the formula: H-D-His-D-Ala-Asp-Gly-Ile-Phe-Asn-Lys-Ala-Tyr-Arg-Lys-Ala-Leu-Gly-Gln-Leu-Ser-Ala-Arg-Lys-Tyr-Leu-His-Thr-Leu-Lys-Ala-Lys-Arg-Val-NH$_2$ is conducted in a stepwise manner using a Beckman 990 Peptide Synthesizer on an MBHA resin as in Example I. The peptide is judged to be substantially pure using TLC and HPLC.

EXAMPLE XVII

The synthesis of the GRF analog peptide having the formula: H-His-Ala-Asp-Gly-Ser-Phe-Asn-Lys-Ala-Tyr-Arg-Lys-Ala-Leu-Gly-Gln-Leu-Ser-Ala-Arg-Lys-Tyr-Leu-His-Thr-Leu-Nva-Ala-Lys-Arg-Val-NH$_2$ is conducted in a stepwise manner using a Beckman 990 Peptide Synthesizer on an MBHA resin as in Example I. The peptide is judged to be substantially pure using TLC and HPLC.

EXAMPLE XVIII

The synthesis of the GRF analog peptide having the formula: N-Et-His-Ala-Asp-Gly-Asn-Phe-Asn-Lys-Ala-Tyr-Arg-Lys-Ala-Leu-Gly-Gln-Leu-Ser-Ala-Arg-Lys-Tyr-Leu-His-Thr-Leu-Val-Ser-Lys-NH$_2$ is conducted in a stepwise manner using a Beckman 990 Peptide Synthesizer on an MBHA resin as in Example I. The peptide is judged to be substantially pure using TLC and HPLC.

EXAMPLE XIX

The synthesis of the GRF analog peptide having the formula: H-His-Ala-Asp-Gly-Asp-Phe-Asn-Ser-Ala-Tyr-Arg-Lys-Ala-Leu-Gly-Gln-Leu-Ser-Ala-Arg-Lys-Tyr-Leu -His-Thr-Leu-Leu-Ala-Lys-Arg-Gln-Gly-NH$_2$ is conducted in a stepwise manner using a Beckman 990 Peptide Synthesizer on an MBHA resin as in Example I. The peptide is judged to be substantially pure using TLC and HPLC.

EXAMPLE XX

The synthesis of the GRF analog peptide having the formula: N-Me-His-D-Ala-Asp-Gly-Met-Phe-Asn-Lys-Ala -Tyr-Arg-Lys-Ala-Leu-Ala-Gln-Leu-Ser-Ala-Arg-Lys-Tyr-Leu -His-Thr-Leu-Nle-Ala-Lys-Gln-Val-NH$_2$ is conducted in a stepwise manner using a Beckman 990 Peptide Synthesizer on an MBHA resin as in Example I. The peptide is judged to be substantially pure using TLC and HPLC.

EXAMPLE XXI

The synthesis of the GRF analog peptide having the formula: H-His-D-Ala-Asp-Gly-Leu-Phe-Asn-Lys-Ala-Tyr-Arg-Lys-Ala-Leu-Gly-Gln-Leu-Ser-Ala-Arg-Lys-Tyr-Leu-His -Thr-Leu-Leu-Ala-Arg-NH$_2$ is conducted in a stepwise manner using a Beckman 990 Peptide Synthesizer on an MBHA resin as in Example I. The peptide is judged to be substantially pure using TLC and HPLC.

EXAMPLE XXII

The synthesis of the GRF analog peptide having the formula: H-His-Ala-D-Asp-Gly-Leu-Phe-Asn-Lys-Ala-Tyr-Arg-Lys-Ala-Leu-Gly-Gln-Leu-Ser-Ala-Arg-Lys-Tyr-Leu-His -Thr-Leu-Nle-Ala-Lys-Arg-Val-Gly-Gly-Gly-Ser-Leu-Ile-Glu -Asp-Asp-Asn-Glu-Pro-Leu-NH$_2$ is conducted in a stepwise manner using a Beckman 990 Peptide Synthesizer on an MBHA resin as in Example I. The peptide is judged to be substantially pure using TLC and HPLC.

EXAMPLE XXIII

The synthesis of the GRF analog peptide having the formula: desNH$_2$-Tyr-Ala-Asp-Gly-Leu-Phe-Asn-Lys-Ala-Tyr-Arg-Lys-Ala-Leu-Gly-Gln-Leu-Ser-Ala-Arg-Lys-Tyr-Leu-Gln-Thr-Leu-Nle-Ala-Lys-Arg-Val-Gly-NH$_2$ is conducted in a stepwise manner using a Beckman 990 Peptide Synthesizer on an MBHA resin as in Example I. The peptide is judged to be substantially pure using TLC and HPLC.

EXAMPLE XXIV

The synthesis of the GRF analog peptide having the formula: N-Ip-Tyr-D-NMA-Asp-Gly-Met-Phe-Asn-Lys-Ser-Tyr-Arg-Lys-Ala-Leu-Gly-Gln-Leu-Ser-Ala-Arg-Lys-Tyr-Leu-His-Glu-Leu-Ile-Ala-Lys-Arg-Val-Gly-NH$_2$ is conducted in a stepwise manner using a Beckman 990 Peptide Synthesizer on an MBHA resin as in Example I. The peptide is judged to be substantially pure using TLC and HPLC.

EXAMPLE XXV

The synthesis of the GRF analog peptide having the formula: desNH$_2$-Tyr-D-NMA-Asp-Gly-Val-Phe-Asn-Lys-Ala-Tyr-Arg-Arg-Val-Leu-Gly-Gln-Leu-Ser-Ala-Arg-Lys-Tyr-Leu-His-Thr-Leu-Gln-Ala-Lys-NH$_2$ is conducted in a stepwise manner using a Beckman 990 Peptide Synthesizer on an MBHA resin as in Example I. The peptide is judged to be substantially pure using TLC and HPLC.

EXAMPLE XXVI

The synthesis of the GRF analog peptide having the formula: D-Tyr-D-NMA-Asp-Gly-Pro-Phe-Asn-Lys-Ala-Tyr-Arg-Lys-Ala-Leu-Gly-Gln-Leu-Ser-Ala-Arg-Lys-Tyr-Leu-His-Thr-Leu-Thr-Ala-Lys-NH$_2$ is conducted in a stepwise manner using a Beckman 990 Peptide Synthesizer on an MBHA resin as in Example I. The peptide is judged to be substantially pure using TLC and HPLC.

All of the synthetic peptides prepared in the Examples are considered to be biologically active and potentially useful for stimulating the release of GH by the pituitary. The minimum effective concentration for the peptides of the Examples is about 1 picomolar.

In vivo experiments inject the synthetic peptides into goldfish after taking blood samples, and additional blood samples are taken 10 and 30 minutes after injections. GH levels in blood, measured by radioimmunoassay, show tha the synthetic peptides of the Examples are active to elevate plasma GH levels when measured at 10 min. after IV injection. Dosages between about 50 nanograms and about 5 micrograms of these peptides per Kg. of body weight are considered to be particularly effective in causing GH secretion. In vitro testing is also carried out using goldfish pituitary cells in primary cultures.

Stimulation of GH secretion by such peptides should result in an attendant increase in growth for fish and other animals with normal GH levels. Moreover, administration should alter body fat content and modify other GH-dependent metabolic, immunologic and developmental processes. These peptides are felt to be particularly useful in aquiculture for raising fish and other cold-blooded marine animals, e.g. sea turtles and eels, and amphibians. Because such GRF analogs also have very low activity in mammalians, these peptides are particularly appropriate for stimulating growth in commercial fish which will be consumed by humans or other mammals because this eliminates the possible problem that residual peptides in the fish might have a biological effect upon the consuming species.

These synthetic peptides or the nontoxic salts thereof may be combined with a pharmaceutically or veterinarily acceptable carrier to form a composition for administration to animals intravenously, subcutaneously, intramuscularly, percutaneously, e.g. intranasally, through the gills or even orally. The required dosage will vary with the particular objective being sought. Moreover, bacteria which have been transformed using recombinant DNA technology to include gene sequences that cause a desired GRF peptide to be expressed can be grown in ponds in which fish are raised to provide such GRF peptides to increase fish growth.

Such peptides are often administered in the form of nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be orally administered in solid form, a binder, such as tragacanth, corn starch or gelatin, and a disintegrating agent, such as alginic acid, may be used. The peptides may also be administered in delayed-release formulations using any suitable agents known in this art. Usually, the dosage used will be from about 0.01 to about 1 microgram of the peptide per kilogram of the body weight of the host.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the peptide chain, particularly deletions beginning at the carboxyl terminal of the peptide and extending to about position-27, can be made in accordance with the known experimental practises to date to create peptides or peptide fragments that retain all or very substantial portions of the biological potency of the peptide, and such peptides are considered as being within the scope of the invention. Moreover, additions may be made to either terminus, or to both termini, and/or generally equivalent residues can be substituted for naturally occurring residues, as is well-known in the overall art of peptide chemistry, to produce other analogs having at least a substantial portion of the potency of the claimed peptide without deviating from the scope of the invention. Moreover, modifications may be made to the preferred $-NH_2$ group at the C-terminus in accordance with the state of this art today, for example, the carboxyl moiety of the amino acid residue at the C-terminus can be the radical $-COOR$, $-CRO$, $-CONHNHR$, $CON(R)(R')$ or $-CH_2OR$, with R and R' being lower alkyl, fluoro lower alkyl or hydrogen, without deviating from the invention for such modifications result in equivalent synthetic peptides.

Various features of the invention are emphasized in the claims which follow.

What is claimed is:

1. A peptide, or a nontoxic salt thereof, having the sequence: $R_1$-$R_2$-$R_3$-$R_4$-$R_5$-Phe-$R_7$-$R_8$-$R_9$-Tyr-Arg-$R_{12}$-$R_{13}$-Leu-$R_{15}$-Gln-Leu-$R_{18}$-Ala-Arg-Lys-$R_{22}$-Leu-$R_{24}$-$R_{25}$-$R_{26}$-$R_{27}$-$R_{28}$-$R_{29}$-$R_{30}$-$R_{31}$-Gly-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-Ser wherein $R_1$ is N-Me Tyr, Tyr, desNH$_2$-Tyr, D-Tyr, N-Et Tyr, N-Ip Tyr, N-Me His, His, desNH$_2$-His, D-His, N-Et His, and N-Ip His; $R_2$ is Ala, D-Ala or D-NMA; $R_3$ is Asp or D-Asp; $R_4$ is Gly or Ala; $R_5$ and $R_{27}$ are selected from the group consisting of Met, Leu, Val, Nva, Gln, Thr, Ile, Ala, Arg, Asn, Asp, Cys, Glu, Gly, His, Nle, Lys, Phe, Pro, Ser, Tyr and Trp; $R_7$ is Asn or Thr; $R_8$ is Lys, Asn or Ser; $R_9$ is Ala or Ser; $R_{12}$ is Lys or Arg; $R_{13}$ is Ala, Val or Ile; $R_{15}$ is Gly or Ala; $R_{18}$ is Ser or Tyr; $R_{22}$ is Tyr or Leu; $R_{24}$ is His or Gln; $R_{25}$ is Thr, Asp, or Glu; $R_{26}$ is Leu or Ile; $R_{28}$ is Ala, Ser or Asn; $R_{29}$ is Lys or Arg; $R_{30}$ is Arg or Gln; $R_{31}$ is Val or Gln; $R_{33}$ is Gly or Glu; $R_{34}$ is Gly, Arg or Ser; $R_{35}$ is Ser or Asn; $R_{36}$ is Met, Leu, Val, Nva, Gln, Thr, Ile or Nle; $R_{37}$ is Ile or Glu; $R_{38}$ is Glu, Gln or Arg; $R_{39}$ is Asp, Arg or Gly; $R_{40}$ is Asp, Ser or Ala; $R_{41}$ is Asn, Arg or Lys; $R_{42}$ is Glu, Phe, Ala or Val; $R_{43}$ is Pro, Asn or Arg; $R_{44}$ is Leu or Ala; provided however that at least one of the following is present: $R_7$ is Asn, $R_8$ is Lys, $R_{13}$ is Ala, $R_{22}$ is Tyr and $R_{25}$ is Thr; and provided further that any or all of the residues after $R_{27}$ may be deleted.

2. The peptide of claim 1 wherein $R_1$ is N-Me His.
3. The peptide of claim 1 wherein $R_1$ is N-Me Tyr.
4. The peptide of claim 1 wherein $R_1$ is N-Et Tyr.
5. The peptide of claim 1 wherein $R_1$ is N-Et His.
6. The peptide of claim 1 wherein $R_1$ is N-Ip His.
7. The peptide of claim 1 wherein $R_2$ is D-NMA.
8. The peptide of claim 1 wherein $R_2$ is D-Ala and $R_3$ is D-Asp.
9. The peptide of claim 1 having the formula: N-Me-His-Ala-Asp-Gly-Met-Phe-Asn-Lys-Ala-Tyr-Arg-Lys-Ala-Leu-Gly-Gln-Leu-Ser-Ala-Arg-Lys-Tyr-Leu-His-Thr-Leu-Met-Ala-Lys-Arg-Val-Gly-Gly-Gly-Ser-Met-Ile-Glu-Asp-Asp-Asn-Glu-Pro-Leu-NH$_2$.
10. The peptide of claim 1 having the formula: N-Et-Tyr-Ala-D-Asp-Gly-Met-Phe-Asn-Lys-Ala-Tyr-Arg-Lys-Ala-Leu-Gly-Gln-Leu-Ser-Ala-Arg-Lys-Tyr-Leu-His-Thr-Leu-Met-Ala-Lys-NH$_2$.
11. The peptide of claim 1 having the formula: H-His-Ala-D-Asp-Gly-Leu-Phe-Asn-Lys-Ala-Tyr-Arg-Lys-Ala-Leu-Gly-Gln-Leu-Ser-Ala-Arg-Lys-Tyr-Leu-His-Thr-Leu-Nle-Ala-Lys-Arg-Val-Gly-Gly-Gly-Ser-Leu-Ile-Glu-Asp-Asp-Asn-Glu-Pro-Leu-NH$_2$.

12. The peptide of claim 1 having the formula: N-Me-Tyr-Ala-Asp-Gly-Nle-Phe-Asn-Lys-Ala-Tyr-Arg-Lys-Ala-Leu-Gly-Gln-Leu-Ser-Ala-Arg-Lys-Tyr-Leu-His-Thr-Leu-Nle-Ala-Lys-NHCH$_2$CH$_3$.

13. The peptide of claim 1 having the formula: H-His-D-Aaa-Asp-Gly-Nle-Phe-Asn-Lys-Ala-Tyr-Arg-Lys-Ala-Leu-Gly-Gln-Leu-Ser-Ala-Arg-Lys-Tyr-Leu-His-Thr-Leu-Met-Ala-Lys-Arg-Val-Gly-Gly-Gly-Asn-Met-Ile-Glu-Arg-Ser-Arg-Val-Asn-NH$_2$.

14. The peptide of claim 1 having the formula: N-Et-His-Ala-Asp-Gly-Met-Phe-Asn-Lys-Ala-Tyr-Arg-Lys-Ala-Leu-Ala-Gln-Leu-Ser-Ala-Arg-Lys-Tyr-Leu-His-Thr-Leu-Met-Ala-Lys-NHCH$_3$.

15. A pharmaceutical composition for stimulating the release of GH in an animal comprising the peptide of claim 1 or a nontoxic salt thereof, and a pharmaceutically or veterinarily acceptable liquid or solid carrier therefor.

16. A method of stimulating the release of growth hormone in an animal, which comprises administering to said animal an effective amount of a peptide, or a nontoxic salt thereof, having the sequence: $R_1$-$R_2$-$R_3$-$R_4$-$R_5$-Phe-$R_7$-$R_8$-$R_9$-Tyr-Arg-$R_{12}$-$R_{13}$-Leu-$R_{15}$-Gln-Leu-$R_{17}$-$R_{27}$-$R_{28}$-$R_{29}$-$R_{30}$-$R_{31}$-Gly-$R_{33}$-$R_{34}$-$R_{35}$-$R_{36}$-$R_{37}$-$R_{38}$-$R_{39}$-$R_{40}$-$R_{41}$-$R_{42}$-$R_{43}$-$R_{44}$-Ser wherein $R_1$ is N-Me Tyr, Tyr, desNH$_2$-Tyr, D-Tyr, N-Et Tyr, N-Ip Tyr, N-Me His, His, desNH$_2$-His, D-His, N-Et His, and N-Ip His; $R_2$ is Ala, D-Ala or D-NMA; $R_3$ is Asp or D-Asp; $R_4$ is Gly or Ala; $R_5$ and $R_{27}$ are selected from the group consisting of Met, Leu, Val, Nva, Gln, Thr, Ile, Ala, Arg, Asn, Asp, Cys, Glu, Gly, His, Nle, Lys, Phe, Pro, Ser, Tyr and Trp; $R_7$ is Asn or Thr; $R_8$ is Lys, Asn or Ser; $R_9$ is Ala or Ser; $R_{12}$ is Lys or Arg; $R_{13}$ is Ala, Val or Ile; $R_{15}$ is Gly or Ala; $R_{18}$ is Ser or Tyr; $R_{22}$ is Tyr or Leu; $R_{24}$ is His or Gln; $R_{25}$ is Thr, Asp, or Glu; $R_{26}$ is Leu or Ile; $R_{28}$ is Ala, Ser or Asn; $R_{29}$ is Lys or Arg; $R_{30}$ is Arg or Gln; $R_{31}$ is Val or Gln; $R_{33}$ is Gly or Glu; $R_{34}$ is Gly, Arg or Ser; $R_{35}$ is Ser or Asn; $R_{36}$ is Met, Leu, Val, Nva, Gln, Thr, Ile or Nle; $R_{37}$ is Ile or Glu; $R_{38}$ is Glu, Gln or Arg; $R_{39}$ is Asp, Arg or Gly; $R_{40}$ is Asp, Ser or Ala; $R_{41}$ is Asn, Arg or Lys; $R_{42}$ is Glu, Phe, Ala or Val; $R_{43}$ is Pro, Asn or Arg; $R_{44}$ is Leu or Ala; provided however that at least one of the following is present: $R_7$ is Asn, $R_8$ is Lys, $R_{13}$ is Ala, $R_{22}$ is Tyr and $R_{25}$ is Thr; and provided further that any or all of the residues after $R_{27}$ may be deleted.

17. A method for growth promotion in aquiculture in accordance with claim 16 by administering to fish or other cold-blooded animals.

18. A peptide, or a nontoxic salt thereof, which is useful in accelerating growth in fish and other cold-blooded animals, which peptide has the formula: $R_1$-$R_2$-$R_3$-Gly-$R_5$-Phe-Asn-Lys-Ala-Tyr-Arg-Lys-Ala-Leu-$R_{15}$-Gln-Leu-Ser-Ala-Arg-Lys-Tyr-Leu-His-Thr-Leu-$R_{27}$-$R_{28}$-$R_{29}$-$R_{30}$-$R_{31}$-NHR wherein $R_1$ is N-Me Tyr, N-Me His, N-Et Tyr, N-Et His, N-Ip His or N-Ip Tyr; $R_2$ is Ala or D-Ala; $R_3$ is Asp or D-Asp; $R_5$ is Met, Nva or Nle; $R_{15}$ is Gly or Ala; $R_{27}$ is Nva or Nle; $R_{28}$ is Ala, Ser, Asn or des-$R_{28}$; $R_{29}$ is Lys or Arg or des-$R_{29}$; $R_{30}$ is Arg or Gln or des-$R_{30}$; and $R_{31}$ is Val or Gln or des-$R_{31}$; and R is H or lower alkyl.

19. The peptide of claim 18 wherein $R_1$ is N-Me His and $R_5$ and $R_{27}$ are Nle.

20. The peptide of claim 18 wherein $R_{30}$ is des-$R_{30}$, $R_{31}$ is des-$R_{31}$ and R is H or ethyl.

* * * * *

UNITED STATES PATENT AND TRADEMARK OFFICE
CERTIFICATE OF CORRECTION

PATENT NO. : 4,784,987
DATED : November 15, 1988
INVENTOR(S) : Jean E. F. Rivier et al.

It is certified that error appears in the above-identified patent and that said Letters Patent is hereby corrected as shown below:

Column 2, line 6, Delete "R-".

Column 9, line 22, Correct the spelling of --resin--.

Column 13, line 3, Change "tha" to --that--.

Column 14, line 13, Before "CON(R)(R')", insert a hyphen ("-").

Column 15, line 6, Change "Aaa" to --Ala--.

Column 15, line 24, Change "$R_1$ $_{27}$" to --$R_{18}$-Ala-Arg-Lys-$R_{22}$-Leu-$R_{24}$-$R_{25}$-$R_{26}$-$R_{27}$--

Signed and Sealed this

Sixteenth Day of May, 1989

Attest:

DONALD J. QUIGG

Attesting Officer

Commissioner of Patents and Trademarks